United States Patent [19]

Edgerton et al.

[11] Patent Number: 4,870,066

[45] Date of Patent: Sep. 26, 1989

[54] METHOD AND COMPOSITION FOR SAFELY DELAYING PARTURITION AND SYNCHRONIZING FARROWING IN SWINE

[75] Inventors: Lee A. Edgerton; Bruce T. Eckerle, both of Lexington, Ky.

[73] Assignee: The University of Kentucky Research Foundation, Lexington, Ky.

[21] Appl. No.: 895,785

[22] Filed: Aug. 11, 1986

[51] Int. Cl.$^4$ .................. A61K 31/56; A61K 31/565; A61K 31/57

[52] U.S. Cl. .................................. 514/169; 514/177; 514/178; 514/179; 514/180; 514/181; 514/182

[58] Field of Search ............... 514/178, 177, 179–182, 514/169

[56] References Cited

U.S. PATENT DOCUMENTS

| | | | |
|---|---|---|---|
| 3,755,574 | 8/1973 | Bertin et al. | 514/182 |
| 3,941,880 | 3/1976 | Short | 514/179 |
| 3,961,053 | 6/1976 | Galantay et al. | 514/178 |
| 4,000,273 | 12/1976 | Grunwell et al. | 260/397.5 |
| 4,073,899 | 2/1978 | Grunwell et al. | 260/397.5 |
| 4,094,977 | 6/1978 | Seeger et al. | 514/171 |
| 4,154,820 | 5/1979 | Simoons | 514/178 |
| 4,237,119 | 12/1980 | Cort et al. | 514/807 |
| 4,283,400 | 8/1981 | von Bittera et al. | 514/177 |
| 4,340,602 | 7/1982 | Brooks | 514/178 |
| 4,686,103 | 8/1987 | Anderson | 514/573 |
| 4,707,492 | 11/1987 | Myers-Keith | 514/450 |

OTHER PUBLICATIONS

Hawley, The Condensed Chemical Dictionary, 10th edition, p. 419.
A. Gooneratne, et al., "Control of Parturition in the Sow Using Progesterone and Prostaglandin", 1979, 32:587–95.
W. Butler, et al., "Plan Your Pigs' Time of Arrival", *Hog Farm Management*, Apr. 1985, pp. 22–23.
M. Dukes, et al., "Effects of Oestradiol and Prostaglandin $F_{2\alpha}$ on the Timing of Parturition in the Rat", 1974, pp. 325–334.
First, et al., "The Endocrine Control of Parturition", pp. 311–342 (1982).

*Primary Examiner*—Cecilia Shen
*Attorney, Agent, or Firm*—King and Schickli

[57] ABSTRACT

A method and composition are provided for extending the gestation period of a sow so as to increase the live birth and survival rates of a swine litter without adversely affecting the sow. The method includes the step of administering an effective dosage of estrogen to the sow 2½–7 days prior to the end of the expected gestation period for the sow. The composition administered includes from 0.5–10 mg of an estrogen selected from a group consisting of estradiol benzoate, estradiol valerate, estrone, estradiol 17$\beta$ and effective mixtures thereof. The composition is adapted for administration parenterally by including a carrier such as corn oil. A method is also provided for synchronizing farrowing in a herd of swine bred following synchronized weaning so as to shorten the target period during which all the sows of the herd begin farrowing. This method involves the administration of a farrowing delaying composition including estrogen as an active ingredient in combination with the administration of an effective dosage of a farrowing inducing composition that may include a prostaglandin as the active ingredient.

15 Claims, 1 Drawing Sheet

DISTRIBUTION OF FARROWING

METHOD        EXPECTED DAY OF FARROWING (A) BRED AT SYNCHRONIZED WEANING (B) BRED AT SYNCHRONIZED WEANING AND INDUCED WITH PGF (C) BRED AT SYNCHRONIZED WEANING AND FURTHER SYNCHRONIZED WITH THE PRESENT METHOD

METHOD AND COMPOSITION FOR SAFELY DELAYING PARTURITION AND SYNCHRONIZING FARROWING IN SWINE

TECHNICAL FIELD

The present invention relates generally to the field of animal husbandry and, more particularly, to methods for both delaying and synchronizing parturition or farrowing in sine. A composition for delaying farrowing is also disclosed and claimed.

BACKGROUND OF THE INVENTION

The economic wellbeing of pork producers not only depends on the cost of feed and the market price for pork, but also on the ability to attain a high percentage of live births and pigs weaned per litter. However, the producer's success for making a profit is contingent on controlling the cost of personnel to assist in the farrowing operation. Thus, maximum utilization of assisting personnel experienced in farrowing is an important factor. Any significant technological advance to improve this factor is assured of being significant to the producer and of receiving wide acceptance.

Having experienced and skilled personnel available to assist during farrowing and the critical neonatal period is critical for several reasons. Often when giving birth to large litters a sow will tire. This can result in the stillbirth of the last few pigs of the litter who are unable to escape the uterus and reach the air before suffocating. Further, pigs are born virtually without hair and, as such, are very susceptible to temperature changes. Colder temperatures can often cause the death of young pigs.

It should also be appreciated that the litter may be larger than the number of functional nipples available on the sow. Nipples on the upper chest are also typically more productive than those at the hindquarter. Thus, small pigs that can't compete with their litter mates may be pushed to the less productive (or even non-productive) nipples and not receive the nutrients needed to grow properly, or possibly not even survive. Specifically, since pigs are not born with but instead receive their immunity through the milk of the sow, undernourished pigs are very susceptible to diseases and infections. Further, even weakened pigs that are able to survive the cold or disease may, however, be slowed and unable to move quickly enough and actually be accidentally crushed by the sow in the pen.

With proper care, it is known that pig survival can be greatly increased. The assisting personnel can help the sow as she farrows thereby keeping her from tiring and reducing the number of stillborn. The personnel can also clean any obstructions such as mucous from the nostrils of newborn pigs to reduce stress and/or even prevent suffocation. Since sows are receptive to pigs even born of another sow, cross-fostering of pigs can be practiced. By evening the number of pigs per sow and placing pigs of approximately the same size with the same sow, better overall nutrition of all the newborn pigs is assured.

From the above it should be appreciated that the concerns of the producer for personnel efficiency and pig survival are essentially in conflict. Recognizing this, producers for a number of years have sought to synchronize farrowing among sows in a herd as much as possible so as to reduce the man-hours required to provide care and increase newborn pig survival.

In the past, synchronized weanings have been used in an effort to synchronize subsequent farrowings. Specifically, after the sows have all been nursing present litters for about three weeks, weaning takes place. Four to six days after weaning, the sows are again ready for breeding. By breeding all the sows on or about the same day, farrowings can be synchronized to fall within a relatively short period.

While this technique is more efficient from the standpoint of utilizing the assisting personnel than random breeding, due to biological variations in time from weaning to estrus and gestation length, the subsequent farrowings of the sows of the herd can still be expected to take place over a period of as much as seven days duration (note FIG. 1, Bar Chart A). Since farrowings can take place any time day or night, assisting personnel may not always be available from the pool of qualified personnel to help the sows and pigs during this extended period and, of course, the cost for round-the-clock attention, if available, is prohibitive. Thus, more effective methods of synchronizing farrowings are desired to further increase labor efficiency and pig survival.

In order to achieve this improved result, it is necessary to either (1) delay the farrowing of those sows that would normally farrow during the early days of this period or (2) induce farrowing of those sows that would normally farrow during the latter days of the period or (3) both delay and induce farrowings as in numbers 1 and 2 above.

It is well known that progestins may be administered to sows late in the gestation period so as to extend gestation and delay farrowing. It is also well established that prostaglandin ($PGF_{2\alpha}$) may be administered to sows so as to induce parturition or farrowing. There, however, are distinct disadvantages to each of these treatments.

The utilization of progestins to delay farrowing has been shown to be effective but with a resulting increase in stillbirths and incidents of dystocia or abnormal labor. Minar, V. M. and E. Schilling, 1970, "Die Beeinflussung des Gerburtstermins Beim Schwein Durch Gestagene Hormone", *Deutsch, Tierarztl,* Wschr. 77:428 and Nellor, J. E., R. W. Daniels, J. A. Hoefer, D. E. Wildt and W. R. Dukelow, 1975, "Influence of Induced Delayed Parturition on Fetal Survival in Pigs", *Theriogenology* 4:23. Because of the increase in stillbirths and the overall reduced survival of the newborn pigs, progestin treatments to delay farrowings are not feasible for utilization in a method to synchronize farrowings where increased pig survival is a desired result.

The utilization of prostaglandin to induce farrowings has also been shown to be effective. The use of prostaglandin to synchronize farrowings in a herd is, however, only of limited effectiveness. Specifically, piglets of induced farrowings born two to three days before the normal term have normal survival and normal birth and weaning weights. Pigs induced to birth more than three days before normal term, however, are underdeveloped at birth and have reduced survival and reduced birth and weaning weights. As such, induced farrowing with prostaglandin can only be effectively utilized to synchronize farrowings without adversely effecting pig survival rates over a three day period. Thus, for a herd of sows bred at synchronized weaning, prostaglandin treatment of only those sows expected to wean on the second through fourth days of the farrowing period is feasible (note FIG. 1, Bar Chart B). A second prostaglandin treatment of those sows expected to wean on days five through seven is, therefore, also necessary if the pig survival rate is to be maintained at a high level. Since a few of the sows also farrow early due to biological variation, personnel must still be available for a large number of hours if the proper care is to be given to the sows and piglets during farrowing and the neonatal period.

A method for both delaying farrowing with progesterone followed by inducing farrowing with prostaglandin to synchronize the farrowings has been proposed by Gooneratne, et al. 1979, in *Control of Parturition in the Sow using Progesterone and Prostaglandin,* Aust. J. Biol. Sci. 32:587. Although these authors claim the procedure has no significant detrimental effects, the incidence of stillbirths from progesterone-treated sows was threefold greater than in untreated sows. Thus, just as discussed above, the utilization of progesterone to delay farrowing is again shown to produce unacceptable survival rates in the newborn pigs. Apparently others have also found this to be true and as a result this method of synchronizing farrowing is not utilized to any significant extent.

A need is, therefore, clearly identified for a safer and more effective method and composition for delaying farrowing in individual sows and for better synchronizing of farrowings throughout the herd.

SUMMARY OF THE INVENTION

Accordingly, it is a primary object of the present invention to provide a method of delaying farrowing and a method of synchronizing farrowing in a herd of sows overcoming the above-described limitations and disadvantages of the prior art.

Another object of the present invention is to provide a safe and effective method and composition for delaying farrowing in sows not adversely affecting the live birth and survival rates of the newborn pigs or the health and subsequent breeding of the sows.

A further object of the present invention is to provide a safe and effective method of extending gestation length so that the resulting newborn pigs have an increased birth weight so as to be stronger with greater energy reserves for improved chances of subsequent survival.

Still another object of the present invention is to provide a more effective method of synchronizing farrowing in sows so as to allow a more efficient and effective utilization of assisting personel and facilities as well as better supervision of sows and newborn pigs during farrowing and the critical neonatal period.

Additional objects, advantages, and other novel features of the invention will be set forth in part in the description that follows and in part will become apparent to those skilled in the art upon examination of the following or may be learned with the practice of the invention. The objects and advantages of the invention may be realized and attained by means of the instrumentalities and combinations particularly pointed out in the appended claims.

In satisfaction of the above objects, the present invention provides a safe and effective method of extending the gestation period of a sow so as to increase the live birth and survival rates of a swine litter without adversely affecting the sow. The method includes the step of administering an effective dosage of estrogen to the sow approximately two and one-half to seven days before the end of the normal gestation period for the sow. In other words, if the normal gestation period for the sow is 115 days, the estrogen should be administered between days 108 and 112.5 of the gestation period. Advantageously, the administration of the estrogen delays the farrowing so that each pig of the litter grows stronger and larger prior to farrowing. Larger and stronger newborn pigs can better withstand stress during the neonatal period with, for example, greater energy stores to survive colder temperatures. Pigs with greater birth weights also tend to have greater weaning weights and are healthier pigs.

More specifically, the effective dosage of estrogen is between approximately 0.5 and 10.0 milligrams. A number of different estrogens may be used effectively and, of course, the dosage required may vary with the estrogen that is used. One example is estradiol benzoate which is administered in a dosage of approximately 3.0 milligrams.

The administration of the estrogen may be performed parenterally by injecting the effective dosage of estrogen with a suitable carrier into the sow. Suitable carriers are substances that do not react with the estrogen and are safe for use in the sow. An example of one such carrier is corn oil.

In accordance with a further aspect of the present invention, a method is provided for substantially synchronizing farrowing in a herd of swine to a single, condensed target period. Preferably, the swine have previously been bred following synchronized weaning for the best results. The method includes the step of administering an effective dosage of a farrowing delaying composition to a first group of sows expected to farrow within substantially 72 hours prior to the target period. As described above, the farrowing delaying composition includes estrogen as an active ingredient. Next is the step of administering before the target period an effective dosage of a farrowing inducing composition to the first group of sows and a second group of sows expected to farrow within substantially 72 hours after the target period. Advantageously, farrowing is then induced in both groups during the target period when labor can be efficiently concentrated so as to allow better care of the sows and pigs and the resulting litters. Thus, by this method, effective utilization of personnel is possible while still providing the sows and newborn pigs with the necessary care to improve overall birth and survival rates. This, of course, results in improved overall economic return for the pork producer.

More specifically, both the farrowing delaying and farrowing inducing compositions include a carrier so as to be adapted for administration parenterally. This allows the injecting of the compositions into the sows. This ensures that each sow is given the correct dosage of the compositions at the proper time.

As described above, the farrowing delaying composition includes approximately 0.5–10 milligrams of estradiol benzoate. This composition is administered to a sow 2½–7 days before the end of the expected gestation.

Preferably, the farrowing inducing composition includes a prostaglandin as an active ingredient. The prostaglandin may also be used in combination with oxytocin. Prostaglandin administration is preferably performed substantially 25–50 hours before the beginning of the target period. Substantially 10.0 milligrams of the prostaglandin $F_{2\alpha}$ (or the dosage recommended by the manufacturers of specific prostaglandin analogues) is administered to each sow. This material is effective in inducing farrowing even in those sows that have already received the estrogen. Thus, farrowing in all the treated sows occurs during a subsequent target period of substantially 24 hours duration (see FIG. 1, Bar Chart C).

In accordance with yet another aspect of the present invention a composition is provided for use in safely delaying farrowing in sows. Advantageously, the composition allows the pork producer to increase the live birth and survival rates of a swine litter without adversely affecting the treated sows. Surprisingly, the composition includes as an active ingredient an effective amount of estrogen. Prior studies on the effects of estrogen during late gestation conclude that estrogen has no effect on gestation length in swine. Previous studies of estrogen treatment of sheep and cattle had actually shown that estrogen induces early parturition. Yet, we have now found that a number of different forms of estrogen can be used to delay parturition when administered during a particular time period, i.e. administered just prior to the end of the expected gestation period. Examples of effective estrogens include estradiol benzoate, estradiol valerate, estrone and estradiol $17\beta$ or any mixtures thereof. The composition may also be adapted for administration parenterally through the provision of a carrier such as corn oil. Other known carriers may, however, be used. Examples of these include peanut oil, olive oil or syrup.

DETAILED DESCRIPTION OF THE INVENTION

As indicated above, the present invention is drawn to a novel method of and composition for delaying farrowing in sows. A novel method of synchronizing farrowings of sows in a herd is also provided.

In order to effectively utilize the methods of the present invention, the pork producer must have knowledge of the expected gestation period of the sows in his herd. The various breeds of swine have normal gestation periods ranging from approximately 112-118 days. Thus, for the sows in a particular producer's herd, the average gestation period may be 115 days. This information is utilized by the producer to institute synchronized farrowings in accordance with the present invention.

Specifically, with the method of the present invention the gestation period of a sow may be extended so as to increase the live birth and survival rates of a swine litter. Advantageously, this is done without adversely affecting the sow. The delay in farrowing is unexpectedly brought about by administering an effective dosage of estrogen to the sow $2\frac{1}{2}$-7 days before the end of expected gestation. The resulting longer gestation means that each pig of the litter is allowed to grow stronger and larger prior to farrowing. Stronger and larger pigs are, of course, better capable of withstanding the stress of birth as well as environmental effects, such as temperature extremes during the neonatal period.

For gilts and sows ranging between approximately 200 and 500 pounds, the effective dosage of estrogen is between 0.5 and 10.0 milligrams. For an average sow, a single injection of substantially 3.0 milligrams of estrogen during the critical time period of $2\frac{1}{2}$-7 days before the end of expected gestation is all that is necessary to extend the gestation period for nearly two days. It should be appreciated, however, that administration of estrogen prior to this critical time frame will have no effect on the length of the gestation period. Further, administration of estrogen after this time frame may, in fact, induce premature farrowing.

A number of different estrogens may be effectively utilized in the method. In particular, estradiol benzoate and estradiol valerate available from a number of sources may be used. Additionally, estradiol $17\beta$ and estrone, both naturally occurring estrogens, may also be used.

Any of these estrogens may be adapted for administration parenterally by forming a composition of the estrogen with an inert carrier that does not react with the estrogens or adversely affect the sow. Corn oil is just one example of such a carrier. This estrogen and corn oil composition may be effectively injected into a sow utilizing a standard syringe.

Figure 1:
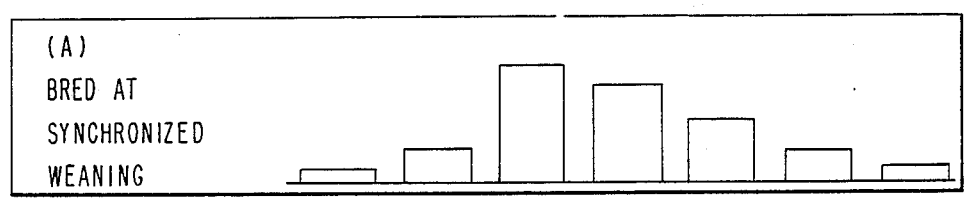
FIG. 1, illustrates the relative effectiveness of synchronized weaning, prostaglandin induced farrowing and the method of the present invention in synchronizing farrowings o sows in a herd.
Figure 1:
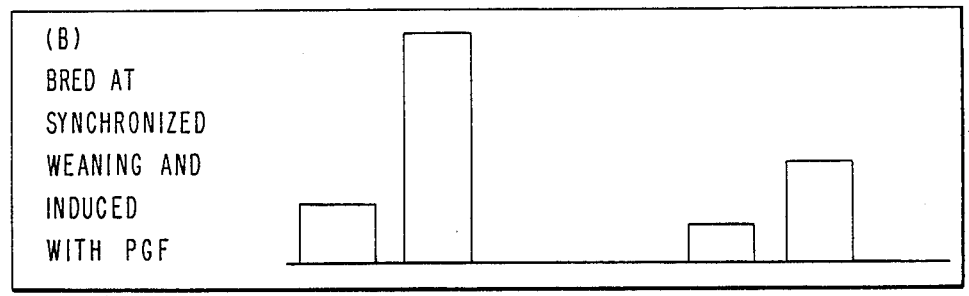
Figure 1:
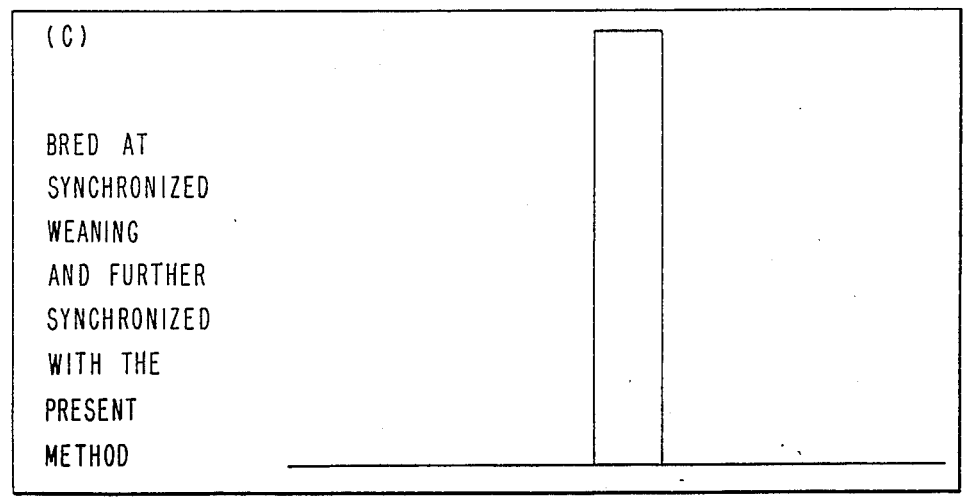

When attempting to synchronize farrowing in a herd of swine bred following synchronized weaning, the estrogen composition discussed above is administered to a first group of sows expected to farrow within substantially 72 hours prior to a selected farrowing target period (i.e. those expected to farrow on any of the first three days of the period shown in FIG. 1.) When administered as described above, the estrogen composition is effective in delaying farrowing in the treated swine for approximately a 40-hour period past the average gestation length. Thus, farrowing in the sows of the first group will not occur until at least the fourth day, as shown in FIG. 1, Bar Chart C. This fourth day is the single, condensed target period upon which this method allows the farrowings of a herd to be synchronized. Approximately 25-50 hours before the beginning of the fourth day, a farrowing inducing composition of prostaglandin is administered not only to the first group of sows but also to a second group of sows expected to farrow within substantially 72 hours after the target period. The sows in this second group would normally be expected to farrow on the fifth, sixth and seventh days.

A number of prostaglandin compounds are known and may be utilized to induce farrowing. These compounds are either the naturally occurring prostaglandin $F_{2\alpha}$ available under the name Lutalyse from the Upjohn Company or analogs of prostaglandin $F_{2\alpha}$ such as Fenprostalene available from Syntex, Inc. or Cloprostenol available from Imperial Chemical Industries. The farrowing inducing effect of the prostaglandin effectively overrides the farrowing delaying effect of previously administered estrogen. Thus, sows of both the first and second groups are induced into farrowing during the condensed target period on the fourth day. Advantageously, by knowing that substantially all the sows of the herd are going to farrow during a period of approximately 24-hours, the pork producer can efficiently provide qualified assisting personnel to aid the sows during birth and 15 care for the newborn pigs during the neonatal period. With this care, both the live birth and survival rates of the newborn pigs are improved. Yet, since the farrowing period is condensed, fewer man-hours are required to provide the necessary care to bring about this improvement. Thus, personnel efficiency is increased so as to improve the economic condition of the pork producer.

The following example is presented to further illustrate the invention, but it is not to be considered as limited thereto.

EXAMPLE 41 sows were randomly allotted to four treatment groups. Group 1 was a control group that received a composition of 2 ml of saline and 1 ml of corn oil. Group 2 received a composition of saline and 3 mg of estradiol benzoate (EB) in corn oil. Group 3 received a composition of corn oil and 10 mg of prostaglanding $F_{2\alpha}$ (PGF). Group 4 received a composition of the combination of EB and PGF also in corn oil. The above compositions were administered parenterally at 8:00 A.M. on day 112 of gestation. The sows were observed every two hours daily with the observers estimating as closely as possible the time of onset and end of farrowing. Other parameters measured during this study were litter size, number of pigs born alive, birth weights, weaning weights at 21 days, and the interval from weaning to estrus for the sows.

The elapsed time from parenteral administration of the above compositions to the onset of farrowing for Groups 1–4 respectively, was 77.3, 117.7, 43.8, and 50.1 hours. The 77 hour period for the control Group 1 placed farrowing for this group at 114.5 days which is the normal, expected time of farrowing for the herd being studied. As should be appreciated, the 117.7 hour period for the EB treated group illustrates a significant extension of the gestation period and delaying of farrowing.

Sows of Group 3 treated with PGF had farrowing induced in 43.8 hours, nearly 33½ hours before the control group. This was expected since PGF has long been known to have a farrowing inducing effect. Lastly, the sows of Group 4 receiving both EB and PGF began farrowing after only 50.1 hours. Thus, farrowing was induced in this group approximately 27.2 hours before the normal farrowing exhibited by the control group. This indicates that PGF overrides the delaying action of EB such that sows treated with the combination of hormones farrowed at a time similar to those treated with PGF alone. This indicates the possibility that one may be able to utilize PGF and estrogen in sequential combination to extend gestation and then induce farrowing synchronously in a group of sows spread over a gestation period anywhere from 112 to 117 days. This is nearly twice the range of days over which farrowing can be synchronized with PGF alone.

The performance characteristics of sows and litters after treatment with EB, PGF or a combination of the two is shown in the table below.

| Treatment* | Duration of Farrowing (h) | Litter Size | % born alive | Weight (lb) Birth | Weaning |
|---|---|---|---|---|---|
| (1) Control | 4.4 ± 4.5 | 11.8 | 90 | 2.60 ± .79 | 15.6 ± 3.3 |
| (2) EB | 3.9 ± 1.8 | 10.4 | 97 | 2.79 ± .70 | 16.1 ± 4.0 |
| (3) PGF$_{2s}$ | 3.8 ± 2.4 | 11.1 | 93 | 2.51 ± .70 | 16.4 ± 4.4 |
| (4) EB & PGF$_{2s}$ | 4.5 ± 3.7 | 12.0 | 94 | 2.40 ± .70 | 15.6 ± 3.2 |

*EB = Estradiol benzoate;
PGF$_{2s}$ = Prostaglandin F$_{2s}$

From a review of this data it is clear that there were no significant differences between the treatment groups for average duration of farrowing. Average litter size was similar for all the groups ranging from 10.4 to 12.0 pigs. It is also clear from the data that extending gestation with EB was not detrimental to the percentage of live births. This is in sharp contrast to the results where gestation is extended utilizing progesterone.

The mean weights at birth and weaning are also comparable. Although the number of litters are two small to statistically detect small treatment effects, the mean of the EB treated Group 2 is numerically greater than that of the control group at both birth and weaning. This indicates that the limited numbers are not masking any detrimental effects on either pre or postnatal development.

Lastly, it is important to note that none of the treatments significantly altered the interval to estrus and rebreeding following weaning. Thus, sows of Group 4 treated with both EB and PGF can be subsequently synchronously bred with sows receiving only PGF, thereby also allowing synchronized farrowings of the next litters when utilizing the present synchronization method.

In summary, numerous benefits have been described which result from employing the concepts of the present invention. A novel method and composition are provided for safely extending gestation in sows. This advantageously allows pigs of the resulting litter to become larger and stronger prior to farrowing. Thus, the rates of live births and survival are improved without adversely affecting the sow during farrowing or subsequent breeding. A method is also provided for synchronizing farrowings of the sows of a herd within a shorter time period. Advantageously, this allows the pork producer to more effectively and efficiently utilize the assisting personnel to provide the care necessary to both the sows and the pigs of the litter to increase newborn pig birth and survival rates. In this way, the pork producer's profitability can be increased.

The invention has been described herein with reference to certain preferred embodiments. However, as obvious variations thereon will become apparent to those skilled in the art, the invention is not be considered as limited thereto.

We claim:

1. A method of extending the gestation period of a sow so as to increase the live birth and survival rates of a swine litter without adversely affecting the sow, comprising the step of administering an effective dosage of naturally occurring estrogen to said sow 2½–7 days before the end of expected gestation, said administration delaying farrowing so that each pig of the litter is allowed to grow stronger and larger prior to farrowing.

2. The method of claim 1, including the step of performing the estrogen administration within the period between days 108 and 112.5 of the gestation period.

3. The method of claim 1, wherein said effective dosage of estrogen is between 0.5 and 10 mg.

4. The method of claim 1, wherein said effective dosage of estrogen is substantially 3.0 mg.

5. The method of claim 1, wherein said estrogen is in the form of estradiol benzoate.

6. The method of claim 1, including of injecting said effective dosage of estrogen with a carrier into said sow.

7. A method of substantially synchronizing farrowing in a herd of swine to a single, condensed target period, comprising the steps of:

administering an effective dosage of a farrowing delaying composition having naturally occurring estrogen as an active ingredient to a first group of sows expected to farrow within substantially 72 hours prior to said target period; and administering before said target period an effective dosage of a farrowing inducing composition having prostaglandin as an active ingredient to said first group of sows and a second group of sows expected to farrow within substantially 72 hours after said target period so as to induce farrowing in both groups during said target period and thereby allow better care of sows and pigs in resulting litters by assisting personnel.

8. The method of claim 7 including of injecting said compositions into said sow, said compositions including a carrier so as to be adapted for administration parenterally.

9. The method of claim 7, wherein said estrogen is estradiol benzoate.

10. The method of claim 8, wherein between 0.5 and 10.0 mg of estradiol benzoate are administered to each sow.

11. The method of claim 7, including of performing said estrogen administration two and one-half of seven days before the end of expected gestation.

12. The method of claim 7, including of performing said estrogen administration between days 108 and 112.5 of the gestation period.

13. The method of claim 7, including of performing said prostaglandin administration substantially 25 to 50 hours before the beginning of said target period.

14. The method of claim 7, wherein substantially 10.0 mg of prostaglandin are administered to each sow substantially 44 hours before said target period.

15. The method of claim 7, wherein said target period is substantially 24 hours in duration.

* * * * *